United States Patent [19]

Wheeler et al.

[11] Patent Number: 4,561,433

[45] Date of Patent: Dec. 31, 1985

[54] INTRAUTERINE DEVICE REMOVER

[75] Inventors: Robert G. Wheeler, Greenbank, Wash.; David M. Potts, Durham, N.C.

[73] Assignee: Family Health International, Research Triangle Park, N.C.

[21] Appl. No.: 645,035

[22] Filed: Aug. 27, 1984

[51] Int. Cl.[4] .............................................. A61F 5/46
[52] U.S. Cl. .................................. 128/130; 128/303 R
[58] Field of Search .................................. 128/127–131, 128/353, 354, 303 R, 304, 330, 357, 756, 759

[56] References Cited

U.S. PATENT DOCUMENTS

| 3,077,879 | 2/1963 | Knoch | 128/130 |
| 3,635,215 | 1/1972 | Shea et al. | 128/130 |
| 3,771,520 | 11/1973 | Lerner | 128/127 |
| 4,227,537 | 10/1980 | Sucia et al. | 128/357 |
| 4,372,302 | 1/1983 | Akerlund | 128/130 |

Primary Examiner—C. Fred Rosenbaum
Assistant Examiner—Karen Kaechele
Attorney, Agent, or Firm—B. B. Olive

[57] ABSTRACT

Apparatus is provided for removing an intrauterine device with a retracted marker tail or an intrauterine device without a marker tail. The device comprises a handle slidably received within a sheath and having resilient bristle means with hooks on the probing end thereof for engaging a retracted tail, or the like.

2 Claims, 5 Drawing Figures

INTRAUTERINE DEVICE REMOVER

DESCRIPTION

1. Technical Field

This invention relates to an improved medical apparatus for removing an IUD from within a uterus via the cervical canal without surgery.

2. Background Art

The most common device used to nonsurgically remove an IUD from within a uterus via the cervical canal consists of a string or marker tail that is attached to the IUD before the IUD is inserted and trails from the IUD through the cervical canal into the vagina when the IUD is in place. When functioning as intended, the IUD is removed by merely gripping the marker tail and pulling it. However, the marker tails sometimes become unattached from the IUD during use or work their way into the cervical canal or uterus. In other instances, they may weaken and break when they are pulled on during the removal procedure.

Removal of IUDs is a serious gynecologocial problem when the marker tails have retracted into the uterus. Also, there is a growing desire to use IUDs with no marker tails, because the tails are thought to increase the incidence of pelvic infection by providing a surface for bacterial ascension into the uterine cavity.

Various retrievers are known in the prior art for removing IUDs. Representative is the apparatus described in U.S. Pat. No. 3,635,215 which comprises an elongated rod with a handle at one end and a hook at the other end and a tube that fits slidably over the rod such that the hook grips the edge of the tube when the rod is slidably moved to its rearwardmost position. This apparatus is inserted through the cervical canal into the uterus and its hook is hooked over the IUD and the snagged IUD is then drawn tightly between the hook and the tube by sliding the rod rearwardly. U.S. Pat. No. 4,022,198 describes an IUD removal apparatus comprised of a rod-shaped handle residing within a tube so that the handle may slide within the tube from a first position to a second position and further comprises a filament extending from the end of the handle which is manipulated so as to entrap an IUD. U.S. Pat. No. 4,372,302 describes an instrument for removal of retracted threads of an IUD wherein the instrument comprises a handle connected to a curved distal portion having a rounded cross section and a concave surface provided with a number of notches adapted for gripping the threads of an IUD. Also, U.S. Pat. No. 3,805,777 describes a rod-like IUD removal device having a magnetic extractor for removal of an IUD formed without a string or tail and with embedded magnets.

All of the known prior art devices, however, are believed to generally suffer from inadequacies in their performance in removing retracted marker tails or in removing IUDs constructed without marker tails. The IUD removal apparatus of the present invention is believed to be superior in performance than any previously-known apparatus.

DISCLOSURE OF INVENTION

The invention is an apparatus for removing an IUD from within the uterus via the cervical canal wherein the marker tails of the IUD have been retracted into the uterus or the IUD incorporates one or more integral filaments or filament-like structure located with the IUD in situ and no marker tails.

Locating and securing IUD marker tails is accomplished with a small cylindrically-shaped bristle brush-like structure on the end of a flexible handle. The bristle brush is preferably formed with each bristle terminating in a hook. The bristles are sheathed within an inserter tube during cervical transit and unsheathed after entry into the uterine cavity. Manual and slow rotation of the retriever while it is moved laterally to explore the endometrial surface causes the hooked bristles to engage and tangle with the retracted IUD strings. Removal of the retriever will expose or make the strings accessible permitting removal of the string-type IUD.

The apparatus is also designed to remove an IUD without marker tails but utilizing one or more filaments extending substantially from the top to the bottom thereof. Since there is a growing desire to use IUDs without marker tails in view of the aforesaid belief that marker tails may increase the incidence of pelvic infection, the successful performance of the instant inventive apparatus on this type of IUD is believed significant. The invention provides a T-shaped IUD without a marker tail but with filaments that can be snagged and particularly suited to the invention.

Therefore, it is an object of the present invention to provide a new and improved device for removing intrauterine contraceptive devices.

It is also an object of the present invention to provide an improved device for removing intrauterine contraceptive devices with retracted marker tails and intrauterine contraceptive devices without marker tails.

Other objects, features and advantages of the present invention will become apparent from the subsequent description and the appended claims, taken in conjunction with the accompanying drawings.

BEST MODE FOR CARRYING OUT THE INVENTION

Figure 1:
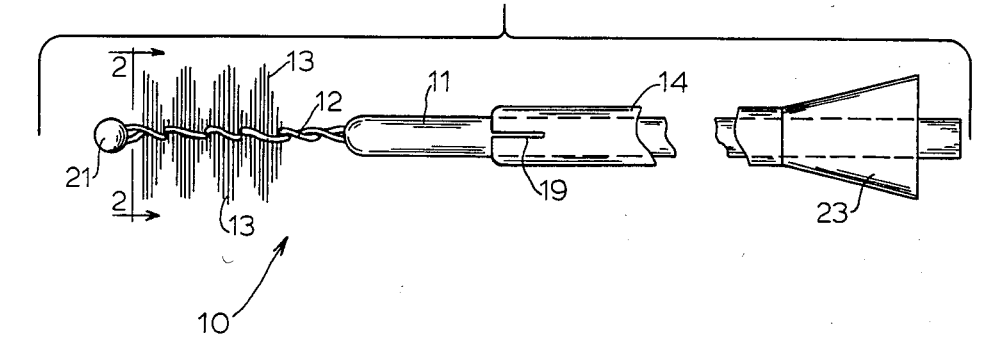
FIG. 1 is a side elevational view of the IUD removal device of the invention.
Figure 2:
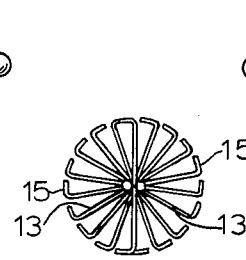
FIG. 2 is an end view of the invention device taken in the direction of line 2—2 of FIG. 1.

Referring to FIG. 1, the preferred embodiment of IUD removal apparatus 10 comprises a handle part 11 which may be stiff but is preferably constructed of a flexible, polymer rod, wire core 12 forming a distal part of handle 11 and preferably constructed of stainless steel wire, bristles 13 which are preferably constructed of nylon monofilament and sheath 14 which is preferably constructed of a flexible polymeric material. As can be best observed in FIG. 1, bristles 13 are twisted within wire core 12 so as to extend radially outwardly therefrom and with the outer ends thereof assuming a helical-like configuration. Also, at least some and preferably each monofilament bristle has a hook 15 (see FIG. 2) on its remote end which extends substantially perpendicularly from the bristle stem and in a generally circumferential direction about the axis of wire core 12. As can be seen in FIG. 2, the radially-extending monofilament bristles 13 are characterized in that hooks 15 are preferably arranged in periodic diametrically opposing relationship to each other so that half the hooks face one direction and half the opposite direction.

Figure 3:
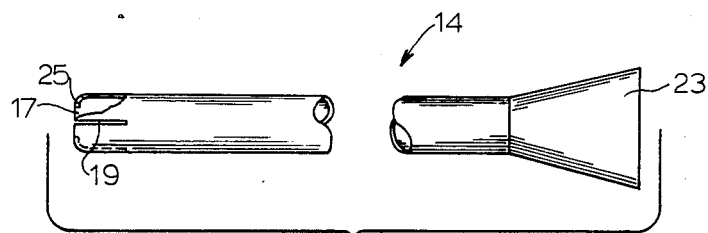
FIG. 3 is a side elevational view, partly in section, of the sheath of the IUD removal apparatus of the present invention.

With reference to FIG. 3, sheath 14 of the present invention is formed with a rounded nosed end 17 surrounding an opening in the probing end thereof and with a plurality of longitudinally-extending slits 19 around the perimeter of the probing end of sheath 14 so as to allow for the ingress and egress of bristles 13.

In construction, bristles 13 were prepared by winding fine nylon monofilament, e.g., 0.006–0.0010" in size, onto a flat strip of stainless steel shim stock about 1 centimeter wide and 10 centimeters long. The monofilament was wound over most of the length of the steel strip with adjacent turns touching. The nylon wound strip was then dipped in a solution of an alcohol soluble nylon, "Elvamid" (manufactured by DuPont), to bond the turns of monofilament together. On one side of the flat steel strip, all of the monofilaments were cut with razor blade close to each edge of the strip. This cutting procedure left a strip of monofilaments with a hook on each end bonded together on the flat steel strip.

To complete the preferred embodiment of hooked bristle brush 13, a strip of the hooked monofilaments about 1 centimeter long was placed between two strands of very small diameter stainless steel wire bent into a hairpin shape. As the two strands of wire were slowly twisted together to form spiral bristles 13, the bristles were washed with alcohol so the individual strands could fan out as depicted in FIG. 1. Twisted wire core 12 was formed around an extension of the axis fo handle 11 and was cemented into an axial hole in the end of handle part 11 using epoxy cement. Handle part 11 was made from a plastic rod 30 centimeters long and 3 millimeters in diameter. A plastic ball 21 was then cemented over the other end of the wire core 12 to prevent the sharp ends of the wire from damaging uterine tissue.

Sheath 14 for bristles 13 and handle part 11 consists of a polyethylene tube with one end nosed over and the other end flared into a funnel shape (FIG. 3) so that bristles 13 with a diameter larger than the bore of sheath 14 may be forced into the sheath. A hot conical steel tool was used to make flare 23, and a round-bottomed hole in a heated polytetrafluoroethylene die was used to produce nosed end 17 and its opening. Nose curvature 25 was produced by pushing the polyethylene sheath tubing into the round-bottomed hole while rotating it by hand. A final step in making sheath 14 consisted of cutting axially-oriented slits 19 in the nosed end of a ninety degree spacing. Slits 19 allow nosed end 17 of sheath 14 to open and expose bristles 13 when the sheath is pulled over the bristles to a retracted position.

Figure 4:
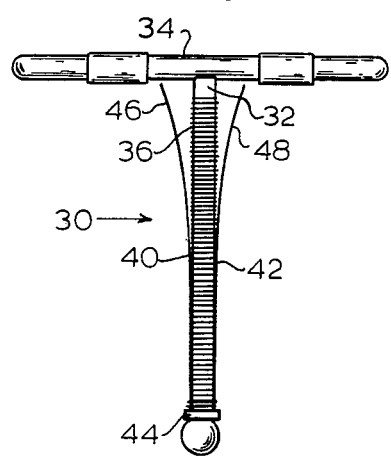
FIG. 4 is an enlarged side view of a stringless Copper-T IUD with a pair of monofilaments suited to being snagged by the device of FIG. 1.

FIG. 4 represents a modified Copper-T IUD 30 having a stem 32, a crossbar 34 and copper wire 36. For purposes of the invention, IUD 30 is fitted with a pair of monofilaments 40, 42 held at the cervix end by a tight band 44 on stem 32 and having unattached free ends 46, 48 directed toward the uterine fundus or cross arm of the IUD but unattached at the fundal end so not to form a closed loop. IUD 30 is intended to be inserted with monofilaments 40, 42 confined within the uterus to avoid the presence of tails. However, when IUD 30 is due to be removed, filaments 40, 42 are readily adapted to be snagged by the device 10 of the invention.

Figure 5:
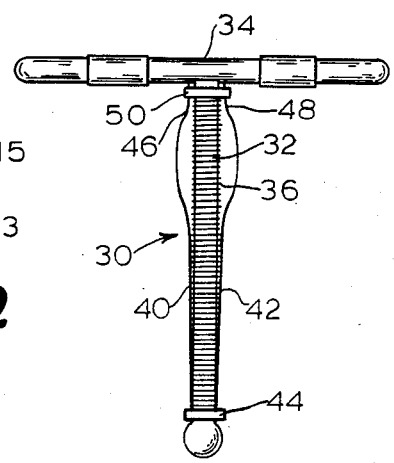
FIG. 5 is a modification of the FIG. 4 IUD in a similar side view.

In an alternative embodiment shown in FIG. 5, the free ends 46, 48 of monofilaments 40, 42 are loosely held by a collar or elastic band 50 to prevent the presence of tails when the IUD is in use to prevent the monofilaments 40, 42 from being expelled into the uterine cervix while still avoiding the hazard of closed loop devices.

In operation, in order to efficiently and atraumatically remove previously-placed IUDs without marker tails and IUDs with retracted marker tails, sheath 14 containing handle distal part 12 with bristles 13 slightly compressed and within the sheath is inserted through the cervix and into the uterine cavity. The plastic ball 21 during entry through the cervix resides within the rounded tube nosed end 17 so as to provide an overall rounded leading surface for entry. After full entry, bristles 13 are unsheathed. Slow manual rotation of handle part 11 while it is moved laterally to explore the entire endometrial surface of the uterine cavity causes hooked bristles 13 to engage and tangle with retracted marker tails or monofilaments utilized on tailess IUDs. After a marker tail on the tail-type IUD or a filament or the like on the tailess IUD, as the case may be, is entrapped, the removal apparatus is withdrawn sufficiently to make the respective tail or filament accessible for subsequent manual withdrawal of the IUD or the removal apparatus itself is used to slowly remove the IUD by pulling on the respective tail or filament.

While the instant invention has been shown and described in what is conceived to be the most practical and preferred embodiment, it is recognized that departures may be made therefrom within the scope of the invention, which is therefore not to be limited to the details disclosed herein but is to be accorded the full scope of the claims so as to embrace any and all equivalent apparatus. For example, distal part 12 and the fiber elements 13 may be molded as an integral element. Alternatively, the fiber elements may be molded as extensions of a set of stacked disks. These and other embodiments will thus appear to those skilled in the art as being within the scope of the invention. While specifically intended for removing an IUD, the device of the invention is also seen as being useful for other operations such as for obtaining cytology specimens, cleaning or scraping of clogged tubular vessels and retrieval of matter from a confined location.

What is claimed is:

1. Apparatus for removing an intrauterine device from a uterus via the cervical canal opening with said device being of the tailess type or of the tail type with the tail retracted in the uterus and in either case having a portion thereof suitably formed for being engaged by a hook to facilitate such removal, said apparatus comprising:
 (a) an elongated handle and a distal part integral therewith, said handle being sufficiently flexible to flex when inserted in the cervical canal opening;
 (b) a hollow, elongated tube mounted and slidable axially on said handle from a first advanced position where said distal part is contained within said tube to a second retracted positon where said distal part extends outwardly from said tube; and
 (c) a plurality of resilient monofilament fiber elements of uniform diameter secured to and extending radially outward from said distal part, each of said elements having a hook formed at the outer end thereof and extending in a generally circumferential direction around the axis of said distal part, said fiber elements including said hooks being compressed within said tube in said tube advanced position and being fully extended and exposed for use in said tube retracted position.

2. An apparatus as claimed in claim 1 wherein at least some of said hooks extend in a substantially opposing direction to others of said hooks.

* * * * *